United States Patent [19]

Shalon

[11] Patent Number: 5,013,433
[45] Date of Patent: May 7, 1991

[54] ZERO VOID COLUMN END PLATE FOR CHROMATOGRAPHY

[75] Inventor: Yehuda Shalon, St. Louis County, Mo.

[73] Assignee: H.T. Chemicals, Inc., St. Louis, Mo.

[21] Appl. No.: 419,086

[22] Filed: Oct. 10, 1989

Related U.S. Application Data

[60] Division of Ser. No. 328,781, Mar. 31, 1989, Pat. No. 4,882,047, which is a continuation of Ser. No. 67,553, Jun. 26, 1987, abandoned, Continuation-in-part of Ser. No. 5,641, Jan. 21, 1987, Pat. No. 4,719,011, which is a continuation of Ser. No. 714,730, Mar. 27, 1985, abandoned.

[51] Int. Cl.$^5$ ............................................. B01D 15/08
[52] U.S. Cl. .................................. 210/198.2; 55/386; 210/456
[58] Field of Search ............... 210/635, 656, 658, 659, 210/198.2, 456; 55/67, 386

[56] References Cited

U.S. PATENT DOCUMENTS

| | | | |
|---|---|---|---|
| D. 28,290 | 8/1986 | Shalon | D10/81 |
| 3,361,261 | 1/1968 | Fairey | 210/314 |
| 3,440,864 | 4/1969 | Blume | 210/198.2 |
| 3,483,986 | 12/1969 | Wright | 210/198.2 |
| 3,879,127 | 4/1975 | Storr | 210/656 |
| 3,904,527 | 9/1975 | Wilhelmson | 210/198.2 |
| 3,966,609 | 6/1976 | Godbille | 210/198.2 |
| 4,079,009 | 3/1978 | Seiler | 210/198.2 |
| 4,263,144 | 4/1981 | Platt | 210/198.2 |
| 4,350,595 | 9/1982 | Gunkel | 210/198.2 |
| 4,354,932 | 10/1982 | McNeil | 210/198.2 |
| 4,399,032 | 8/1983 | Mott | 210/198.2 |
| 4,469,597 | 9/1984 | Mott | 210/198.2 |
| 4,512,897 | 4/1985 | Crowder | 210/198.2 |
| 4,557,830 | 12/1985 | Onitsuka | 210/198.2 |
| 4,582,608 | 4/1986 | Ritacco | 210/656 |
| 4,587,014 | 5/1986 | America | 210/198.2 |
| 4,627,918 | 12/1986 | Saxena | 210/656 |
| 4,636,315 | 1/1987 | Allen | 210/198.2 |
| 4,675,104 | 6/1987 | Rai | 210/198.2 |
| 4,675,105 | 6/1987 | Martin | 210/198.2 |
| 4,719,011 | 1/1988 | Shalon | 210/198.2 |
| 4,891,133 | 1/1990 | Colvin | 55/386 |
| 4,894,152 | 1/1990 | Colvin | 55/386 |

FOREIGN PATENT DOCUMENTS

| | | | |
|---|---|---|---|
| 1773578 | 10/1971 | Fed. Rep. of Germany | 210/198.2 |
| 2409935 | 9/1974 | Fed. Rep. of Germany | 210/198.2 |
| 210212 | 6/1984 | German Democratic Rep. | 210/198.2 |

OTHER PUBLICATIONS

Snyder, Introduction to Modern Liquid Chromatography, John Wiley & Sons, Inc., New York, 1979, pp. 207-210.

Primary Examiner—Ernest G. Therkorn
Attorney, Agent, or Firm—Sandler, Greenblum & Bernstein

[57] ABSTRACT

In chromatography columns, a pair of end plates mounting upon integral column flanges provided at either end of said chromatography column, each end plate mounting a series of frits and O-rings in place within cylindrical grooves provided within each end of the column, each end plate arranged contiguously with the enclosed frits incorporating a series of radially disposed grooves, to provide for dissemination of the incoming chemicals uniformly about the entire cross-section of the column chamber, to provide for efficient dispersion of said chemicals throughout the entire slurry packing contained therein, and incorporating equivalent grooves upon the inner surface of the end plate connecting with the outlet end of the column, to assure uniformity of collection of the chromatography treated chemicals as they are discharged to a location for usage or collection.

5 Claims, 1 Drawing Sheet

ZERO VOID COLUMN END PLATE FOR CHROMATOGRAPHY

This is a division of U.S. application Ser. No. 07/328,781 filed Mar. 29, 1989, now U.S. Pat. No. 4,882,047, which is a continuation of Ser. No. 07/067,553 filed on June 26, 1987, now abandoned, which is a continuation-in-part of Ser. No. 07/005,641 filed Jan. 21, 1987, now U.S. Pat. No. 4,719,011, which is a continuation of Ser. No. 06/714,730 filed Mar. 22, 1985, now abandoned.

BACKGROUND OF THE INVENTION

This invention relates generally to a high pressure liquid chromatography column, and more specifically such a column incorporating an end plate(s) which is structured at the column entrance to provide optimal fluid distribution at the fluid entrance into the column, and may likewise incorporate similar operative structure to provide for uniform discharge of fluid from the said column, at its outlet end.

In a separation column, principally used in preparative HPLC, it is important for the fluid to be uniformally distributed throughout the cross-sectional area of the separation medium, compacted within the column, in order to insure efficient operation of the column and to attain accurate results. Generally, if there is no method or means to disperse the incoming fluid at the entrance, or at the top of the column, the fluid to be separated will not be evenly distributed throughout the cross-sectional area of the column until it reaches some considerable depth within the column, below its entrance, thereby causing the column to operate rather inefficiently. It is the purpose of this current invention to construct a column so that the fluid will enter the column evenly and be distributed throughout the crossectional area of the separation media, at the entrance, thereby further attaining uniform distribution of the incoming fluid throughout the length of the column, in order to attain most effective chromatography results particularly when used for preparative purposes.

Previous inventors have addressed this problem, as for example, as shown in U.S. Pat. No. 4,582,608. But, while assuming that effective results are attained through the structure as shown in the identified patent, it is to be noted that in order to attain such distribution a multi-component entrance means in the form of precisely manufactured distributor plate, used in combination with wire mesh disk, and applied in conjunction with a frit, and further incorporating a disburser plate, all as located within a specially designed and provided conical recess within the column end closure, must be structured into that defined embodiment in order to attain its desired distribution of fluids throughout the media within its column. Hence, while the device of this earlier patent might attain effective results, as explained in the patent, there is concern with the multiplicity of components that must be assembled together within the structure during its fabrication, in order to attain any desired results.

Hence, it is the principal object of the current invention to provide designed flow paths structured into the inner surface of the end closure for an HPLC column, and which automatically provides for dispersal of the incoming fluid throughout the cross-section at the entrance of the column, so that the fluids will be subjected to the entire media contained within the column, in order to attain uniform operation and most effective results during the performance of any chromatography process.

Another object of this invention is to provide a series of radially disposed precisely dimensioned grooves that are milled and formed within the enclosure of a chromatography column in order to attain adequate distribution of any incoming chemical.

It is a further object of this invention to provide a uniquely designed fitting or adapter, that may locate both within the entrance closure plate, or at the exit closure plate, to effectively achieve convenient conveyance of chemicals passing through the chromatography column.

Another object is to provide an especially designed frit for use in conjunction with chromatography, and which augments the uniform distribution of the incoming chemicals over the entire cross-section of the separation media contained within the column.

These and other objects will become more apparent to those skilled in the art upon reviewing the summary of this invention, and while undertaking a study of the description of its preferred embodiment in view of the drawings.

SUMMARY OF THE INVENTION

This invention contemplates an open ended, cylindical media chamber as at C, uniform in diameter, functioning as a chromatography column, and incorporating, preferably, integrally protruding flanges on either end to which the top and bottom end or closure plates are secured. The inside face of the end plates, and particularly the entrance closure plate, incorporates a grooved surface, with the grooves being generally radially disposed, and increasing in width and depth as they radiate outwardly from the center of the cover, forming a dispersion chamber integrally structured within the plate, to facilitate the prompt distribution of incoming chemicals, and also their collection at the end of the column, during the performance of a chromatography procedure therein. These radially disposed grooves, in their composite, have a diameter somewhat equal to the diameter of the interior of the media chamber C contained within the chromatography column. The purpose of the dispersion chamber, formed of these radially disposed grooves, is provided for creating a uniform distribution of the entrant chemicals delivered into the chromatography column, during its functioning. To provide a proper seal at the location of the closure plates, each flange of the column, and perhaps even a corresponding inner surface of the closure plate, may incorporate an annular or cylindrical depression or groove, and into which may fit a sealing O-ring. In addition, each flange of the cylinder incorporates a cylindrical depression, forming a shoulder, and into which fits one or more frits, and cooperating O-ring(s), in order to provide a proper mount for the initial separation and dispersion structure at this location. Preferably, a pair of frits will locate at the entrance end of the column, and likewise, a pair of similar type frits will locate at the exit end of the column. The pairs of frits are maintained contiguously, with the outside frit at both ends of the column preferably having a non-porous formed, depressed, circular center to further aid in the uniform distribution and flow radially outwardly of the incoming chemicals, in order to augment the dispersion of the chemicals passing through the column during its operation. Each end plate incorporates a centrally located, threaded orifice, and into which a tubing form of adapter threadedly engages, or otherwise fits, in order to accommodate the flow of chemicals into the column, and likewise, their exit therefrom. The tubing adapters are provided with a circular groove, upon its end plate contacting form shoulder, arranged concentrically around the screw portion of the adapter, and into which fits an O-ring or other seal for the purpose of providing a fluid tight seal between the tubing adapter, and the respective end or closure plate upon which it mounts.

DESCRIPTION OF THE PREFERRED EMBODIMENT

Figure 1:
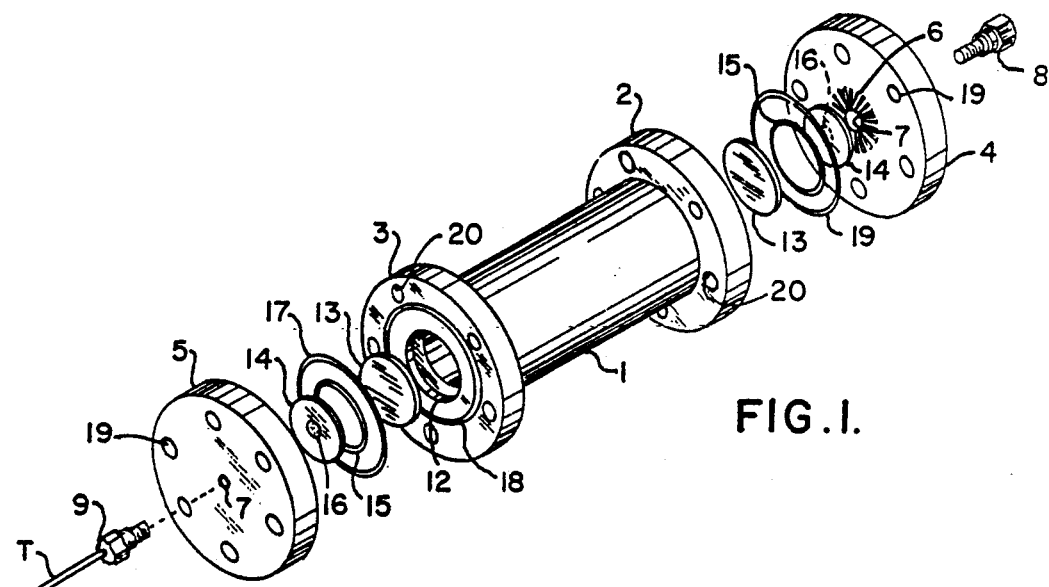
FIG. 1 is an isometric and exploded view of the HPLC column complete with its tube adapters, dispersion grooves, frits, and O-rings, all mountable upon the column structure.
Figure 2:
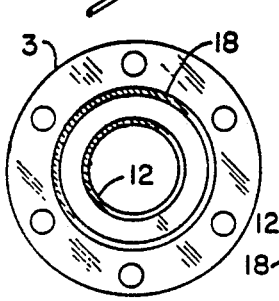
FIG. 2 is an end view of the column bottom flange as viewed from the left.
Figure 3:
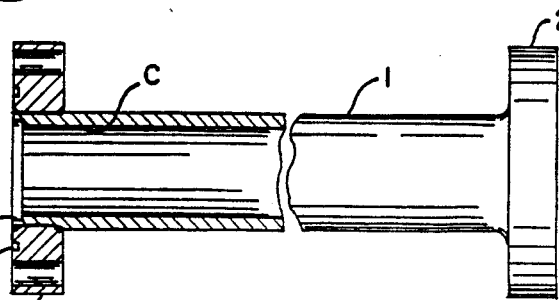
FIG. 3 is a side view, with a partial cross-sectional view, of the media chamber for the column.
Figure 4:
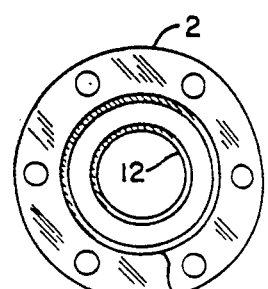
FIG. 4 is an end view of the column flange at its entrance end as viewed from the right for the column of FIG. 3.

In referring to the drawings, an in particular FIG. 1, an in accordance with the purpose of this invention, the chromatography column 1 incoporates, preferably, integrally, a pair of flanges 2 and 3, said flanges, respectively, generally identified herein as the entrance flange, and the exit flange, for the column structure. Mounting onto each of the flanges, respectively, is an entrance end or closure plate 4 and an exit end or closure plate 5 as can be seen. Generally, these end plates are fabricated identically in structure, and mount or are held into contiguity within the structure of the assembled column with the related type of components as to be hereinafter defined. The end plates each have been constructed so that the entrant chemicals will be conviently dispersed throughout the full cross-sectional area of the separation media contained within the column, upon entry of the chemicals into the column during performance of a chromatography process. The object of the invention, as previously alluded to, is to avoid any band spreading of chemicals during the performance of a critical separation process. Furthermore, usage of the type of column incorporating the zero void end plates of this invention is recommended when the column contains slurry packing particles less than twenty microns in diameter.

Figure 5:
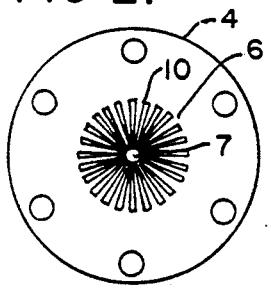
FIG. 5 is a plan view of the inside face of the top end plate.
Figure 7:
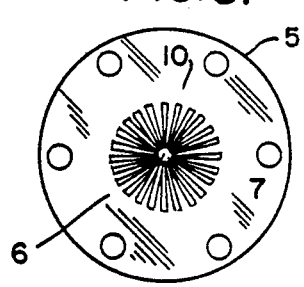
FIG. 7 is a plan view of the inside face of the bottom end plate.
Figure 9:
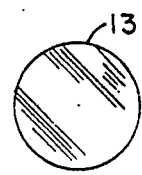
FIG. 9 is a plan view of the top or bottom inside frit.
Figure 11:
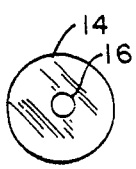
FIG. 11 is a plan view of the outside frits utilized in this structure.

To achieve the foregoing, the column 1 incorporates its end plates 4 and 5, and each end plate has a series of radial grooves on their inner face, as at 6, to evenly disperse the flow of chemicals entering into the column, at the entrance end, and likewise to provide for uniformity of collection of the same, as at the exit or outlet end of the column. FIGS. 5 and 7 disclose these inner surfaces for each of the end plates, showing the disposition of the radially formed grooves that function for the purposes as previously described. Generally, to provide a little more detail relating to these plate structures, each end plate, in the preferred embodiment, is formed of 0.625 inch thick material, and incorporates a threaded orifice, as at 7, centrally therethrough. Obviously, this dimension is only illustrative, and other dimensions can be used. It is into this orifice that the tubing adapter 8 threadily engages within the end plate 4, and likewise, a related type of adapter, as at 9, threadily engages within the exit end plate 5, as can be noted.

Figure 6:
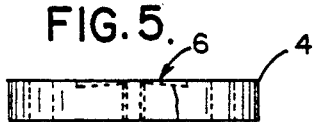
FIG. 6 is a side view of the end plate shown in FIG. 5.
Figure 8:
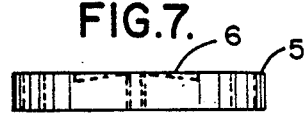
FIG. 8 is a side view of the bottom end plate disclosed in FIG. 7.
Figure 10:
FIG. 10 is a side view of the inside frit of FIG. 9.
Figure 12:
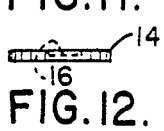
FIG. 12 is a side view of the frit disclosed in FIG. 11.
Figure 16:
FIG. 16 is a plan view of the bottom of the tubing adapter disclosed in FIG. 13.

As can be further seen, the inside face of each of the end plates incorporating these radial grooves has grooves that are particularly designed so as to augment the dispersal flow of the incoming chemicals, or collection to the same, during chromatography processing. For example, in referring to the combination of FIGS. 5 and 6, or FIGS. 7 and 8, the respective end plates show that the grooves are of increasing dimension, as they radiate outwardly from their central communication with the orifice or port 7. As can be seen, these grooves are of greater width, as at 10, than they are at their central location. Furthermore, as can be seen in FIGS. 6 and 8, these grooves 6 are formed deeper, as at 11, at their outermost location, and thus, as can be readily understood, the grooves, in general, as previously explained, have greater capacity as they extend further outwardly from their communication with their orifices 7. Thus, the incoming chemicals are easily urged to radiate outwardly, within these formed grooves of each of the end plates, as the chemicals flow into the column, as through the top end plate 4, and likewise said chemicals attain easy access into the same grooves, at their outermost perimeter, as the chemicals are collected for flow through the end plate 5, for exit after being processed during passage through the column 1. To be more specific, these grooves increase in width as they radiate outwardly, at an angle of approximately 0.705 degrees (the angle formed by the midline and the outer edge of the groove) and they increase in depth by an angle of approximately 2.4 degrees (the angle being formed by the inside face of the plate and the innermost surface of the formed grooves). Obviously, other dimensions for angles and number of grooves applied may vary according to design specifications.

The cylindrical flanges 2 and 3 provided on either end of the column 1 incorporate cylindrical like depressions or counterbores, one as shown at 12, on either end, proximate the column media chamber C, and these depressions generally are cut to form a shoulder at each end, approximately 0.114 inches deep, and into which are placed the various frits 13 and 14, and an O-ring 15, to provide for convenient seating of said frits in place, particularly for sealing the regular frit 13 in place.

Other dimensions for shoulder depth could be utilized. Such a combination is provided at each end of the column, as can be noted in FIG. 1. These frits are nomally constructed as standard type of frits that are currently available in the art, but in the preferred embodiment, the outer frits 14 for this development have a depressed and compacted center portion, as at 16, and which are designed to provide a dense area that does not allow the passage of the liquid chemicals therethrough, but rather, forces the same laterally thereof, to assure proper dispersion and spread of the chemicals as the same enters into the column, and likewise to provide for uniformity of collection of the chemicals as at the outlet end. On the other hand, in the preferred embodiment, it is just as likely that the depression 16 provided within the frit 14 located at the exit from the column may not contain such a depression, since the need for spread of the chemicals proximate the outlet is not as great as that sought from the entrance end of this column, for reasons as previously described. In structure, each inner frit 13 has a radius equal to the radius of the media chamber, and formed counterbore or shoulder 12, and has rested upon it the contiguous outer frit 14, which has a radius approximately less than the radius of the shoulder, as to be described. The outer frit is held in place within the O-ring 15, to provide for a snug containment of said frits together, and with the O-ring, into position within their respective column ends, and upon the formed chamber shoulder. Generally, the density of the inner frits 13 is determined in accordance with the media particle size used in the column. In addition, the density of the outer frits 14 is usually established high, in order to effectively achieve dispersion of the chemicals passing into and through the column.

In addition to the foregoing, another O-ring, as at 17, is designed for fitting within the grooves 18, formed within the external surfaces of the flanges 2 and 3, in order to assure fluid tight seal between the end plates 4 and 5, and their respective flanges for the column 1.

It is to be noted there are a series of aligned apertures, as at 19, provided through each of the end plates, and likewise there are a series of aligned apertures, as at 20, provided through each of the column flanges, and these apertures in their alignment are for retention of fasteners (not shown) therethrough, as when it is desired to close off the column in preparation for its usage in chromatography.

Figure 15:
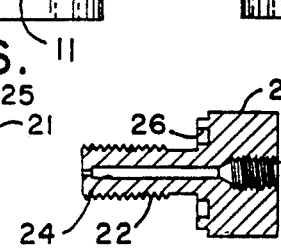
FIG. 15 is a longitudinal cross-sectional view of the tubing adapter disclosed in FIG. 13.
Figure 14:
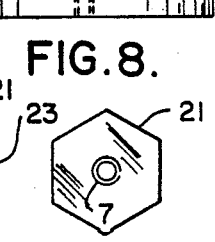
FIG. 14 is a top plan view of the tubing adapter of FIG. 13.
Figure 13:
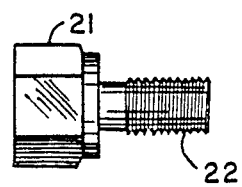
FIG. 13 is a side view of the entrance and exit tubing adapter.

The tubing that conducts chemicals to the column, and likewise, carries it therefrom, is connected to the column by means of the adapters 8 and 9, as previously explained. These adapters screw into the threaded orifices provided through each of the end plates, as noted. The head of each adapter is formed as a hex, as shown at 21, having an integrally extending and threadily formed body portion 22, as noted. The tubing T conducting chemicals to or from each adapter threadily engages by means of another fitting within the threaded interior, as at 23, for each adapter. A conduit 24 provides for flow of the liquid chemicals therethrough. The bottom surface of each of the heads 21 of the adapter incorporate an annular groove, as at 25, therein, as can be seen in FIG. 15, and each groove is designed to accommodate an O-ring, seal, or other means, that provides for a tight fitting of each adapter in place, within its respective end plates 4 or 5, when tightened into their operative positions. This seal, which fits within the groove 25, tightly binds against the external surface of either end plate 4 or 5, when the adapter are secured into position.

Variations or modifications to the structure of this invention may occur to those skilled in the art upon reviewing the structure of this embodiment as explained herein. Such variations or modifications, if within the spirit of this invention, are intended to be encompassed within the scope of any claims to patent protection issuing upon this development. The description of the preferred embodiment set forth is done so primarily for illustrative purposes only.

I claim:

1. A fluid dispersion apparatus comprising:
   (a) an end plate, said end plate having an inlet port and fluid dispersion means, said dispersion means comprising a plurality of grooves on the surface of said end plate proximate said frit means, said grooves extending radially towards the periphery of said plate and increasing in volume in a direction towards the periphery of said plate, each of said grooves increasing in depth in a direction towards the periphery of said plate and also increasing in width in a direction towards the periphery of said plate, wherein the surface of said end plate proximate said frit means has no other grooves thereon; and
   (b) frit means, said frit means being mounted proximate said end plate, said frit means being porous and providing for fluidic communication between said inlet port and an interior chamber, said frit means including a porous member substantially entirely formed with interconnecting pores for the passage of fluids, except for a central high density region which does not allow the passage of fluids through said region.

2. The fluid dispersion apparatus of claim 1, wherein each plate has twenty-four grooves radially spaced around the center of the end plate.

3. The fluid dispersion apparatus of claim 2, wherein adjacent grooves are separated from each other by approximately fifteen degrees.

4. The fluid dispersion apparatus of claim 1, wherein said frit means comprises an inner and an outer porous frit, said inner porous frit providing for fluid communication, said outer frit means being proximate said end plate and substantially entirely formed with interconnected pores for the passage of fluids except for a central high density region which does not allow the passage of fluids.

5. The fluid dispersion apparatus of claim 4, wherein said outer frit has a high density center depression formed therein.

* * * * *